US00PP23869P3

(12) United States Plant Patent
Patrick, Jr.

(10) Patent No.: US PP23,869 P3
(45) Date of Patent: Sep. 3, 2013

(54) BOXWOOD PLANT NAMED 'THOMAS JEFFERSON'

(50) Latin Name: *Buxus sempervirens*
Varietal Denomination: Thomas Jefferson

(75) Inventor: Thomas M. Patrick, Jr., Greenville, SC (US)

(73) Assignee: Saunders Brothers, Inc., Piney River, VA (US)

( * ) Notice: Subject to any disclaimer, the term of this patent is extended or adjusted under 35 U.S.C. 154(b) by 245 days.

(21) Appl. No.: 11/655,489

(22) Filed: Jan. 16, 2007

(65) Prior Publication Data

US 2008/0184411 P1 Jul. 31, 2008

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Kent L Bell
(74) *Attorney, Agent, or Firm* — Buchanan Ingersoll & Rooney PC

(57) ABSTRACT

A new and distinct ornamental Boxwood plant is provided which originated as a chance seedling of unknown parentage. The plant displays a pronounced substantially uniform upright growth habit in the absence of pruning. Throughout the year, rich deep green leaves having a glossy upper surface are exhibited in the substantial absence of winter bronzing. The branches are of superior strength and commonly will resist snow and ice damage during winter months. Good resistance to disease and pests also is displayed. The plant is well suited for providing attractive ornamentation in the landscape. For instance, it can be grown as a specimen or accent plant, as a tall hedge, or when present in a container in a patio setting, etc.

7 Drawing Sheets

Botanical/commercial classification: *Buxus sempervirens*/ Boxwood Plant.

Varietal denomination: cv. Thomas Jefferson.

BACKGROUND OF THE INVENTION

Boxwood plants have been grown for centuries to provide attractive ornamentation, and commonly are associated with plantings indicative of distinction and nobility. Among these is *Buxus sempervirens* or Common Boxwood which often has been grown in North American gardens from colonial times forward.

The new Boxwood plant of the present invention was discovered in 1964 while growing as a chance seedling in a garden cultivated and tended by man at Charlottesville, Va., U.S.A. *Buxus sempervirens* or Common Boxwood plants were prominently being grown in the garden where the new plant was discovered. While the exact parentage of the found plant is unknown, the plant is a new cultivar of *Buxus sempervirens*. The plant of the present invention was selected and has been carefully preserved in view of its distinctive combination of characteristics. Upon transplanting to South Carolina, the unique combination of plant characteristics has been carefully observed and has been confirmed. Had the plant not been discovered and preserved, it would have been lost to mankind.

It was found that the new Boxwood plant of the present invention displays the following combination of characteristics:

(a) displays a pronounced upright growth habit,
(b) displays throughout the year attractive deep green leaves having a glossy upper surface in the substantial absence of winter bronzing, (c) forms branches of superior strength that commonly will resist snow and ice damage during winter months,
(d) displays good resistance to disease and insects, and
(e) is particularly well suited for providing distinctive ornamentation in the landscape.

The new cultivar well meets the needs of the horticultural industry as a quality woody ornamental. The upright growth habit combined with other characteristics renders the plant well capable of being grown as an ornamental specimen or accent plant at the end of a walkway or as a foundation plant at the corners of a residence or other building. Additionally, it can be grown to advantage as a tall hedge or in containers or pots in a patio setting, etc. The foliage also can serve as a holiday decoration.

The plant performs well while utilizing conventional cultural practices for the growth of Boxwood. Good winter hardiness has been observed. The plant performs best in well drained soil. The plant additionally has not been subject to damage by deer.

The ability of the new plant to well withstand common Boxwood pests and diseases during observations to date has been noteworthy and thereby is capable of providing a significant benefit to Boxwood growers.

The new plant can be readily distinguished from Common Boxwood, as well as all other upright commercially available Boxwood cultivars. More specifically, Common Boxwood commonly displays a dissimilar somewhat spherical non-upright growth habit. Significant differences also are apparent when compared to the upright 'Dee Runk' and 'Green Mountain' Boxwood cultivars (both non-patented in the United States). The 'Dee Runk' cultivar is a considerably more rapid grower and displays considerably less sturdy branches than the new cultivar. The 'Green Mountain' cultivar displays an upright habit that commonly is broader at the base, is less uniform, and is more informal in overall appearance. Also, the branches of 'Green Mountain' are less rigid, and the leaves of 'Green Mountain' are less glossy and commonly are lighter green in coloration particularly during the winter.

Asexual reproduction of the new cultivar has been carried out at Greenville, S.C., U.S.A., and Piney River, Va., U.S.A. Such propagation has included the use of stem cuttings and layering. Stem cuttings can be taken after new growth has hardened in late summer into winter and thereafter caused to root with the aid of a growth hormone in accordance with conventional techniques. The asexual propagation has confirmed that the unique combination of characteristics of the new cultivar is stably established and is well transmitted to successive generations. The new cultivar asexually reproduces in a true-to-type manner.

The new plant has been named 'Thomas Jefferson' in view of our third President's association with Charlottesville, Va., U.S.A., where the new plant was discovered.

BRIEF DESCRIPTION OF PHOTOGRAPHS

The accompanying photographs show, as nearly true as it is reasonably possible to make the same in color illustrations of this character, typical specimens of the new cultivar, as well as typical specimens of comparative previously available upright Boxwood cultivars. The plants had been asexually reproduced by the rooting of cuttings and were being grown in full sun during November except as otherwise indicated at Piney River, Va., U.S.A.

FIG. 1 illustrates the substantially uniform upright growth habit of a typical plant of the new cultivar at the age of approximately 12 years. Such plant was approximately 5 feet in height and approximately 2 feet in width at the widest point.

FIG. 2 illustrates for comparative purposes a typical upright plant of the 'Green Mountain' cultivar at an age of approximately 12 years. It will be noted that the plant width is significantly broader at the base. Such plant was approximately 5½ feet in height and approximately 4 feet in width at the widest point.

FIG. 3 illustrates for comparative purposes a typical upright plant of the 'Dee Runk' cultivar. The branches initially emerge from stems at a lesser angle than those of the new cultivar and are less sturdy. The illustrated plant was approximately 12 years of age, approximately 6½ feet in height, and approximately 2½ feet in width at the widest point. The 'Dee Runk' cultivar is a more rapid grower than the new cultivar of the present invention.

Figure 7:
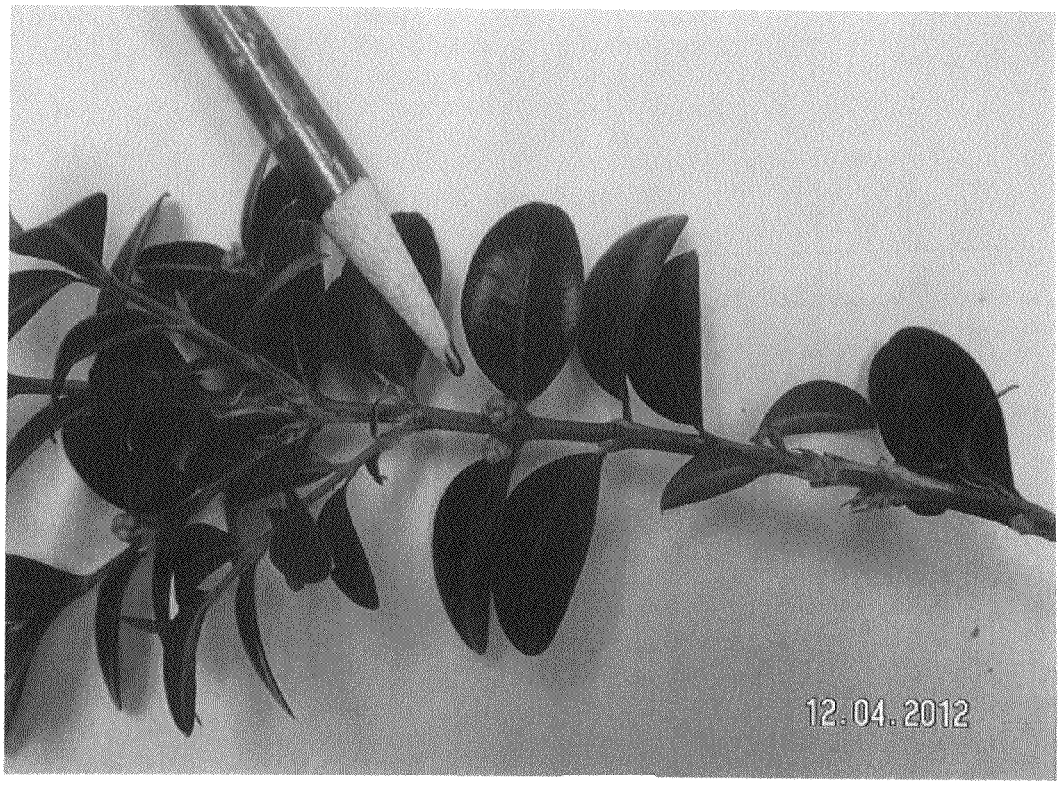

FIG. 7 illustrates a one-year-old branch of the new cultivar in which a typical light brown floral bud is identified by pointing. Such floral buds rarely are encountered, are believed to form flowers comparable to those of *Buxus sempervirens* Common Boxwood, and will open during the subsequent spring. This photograph was prepared during early December.

Figure 8:
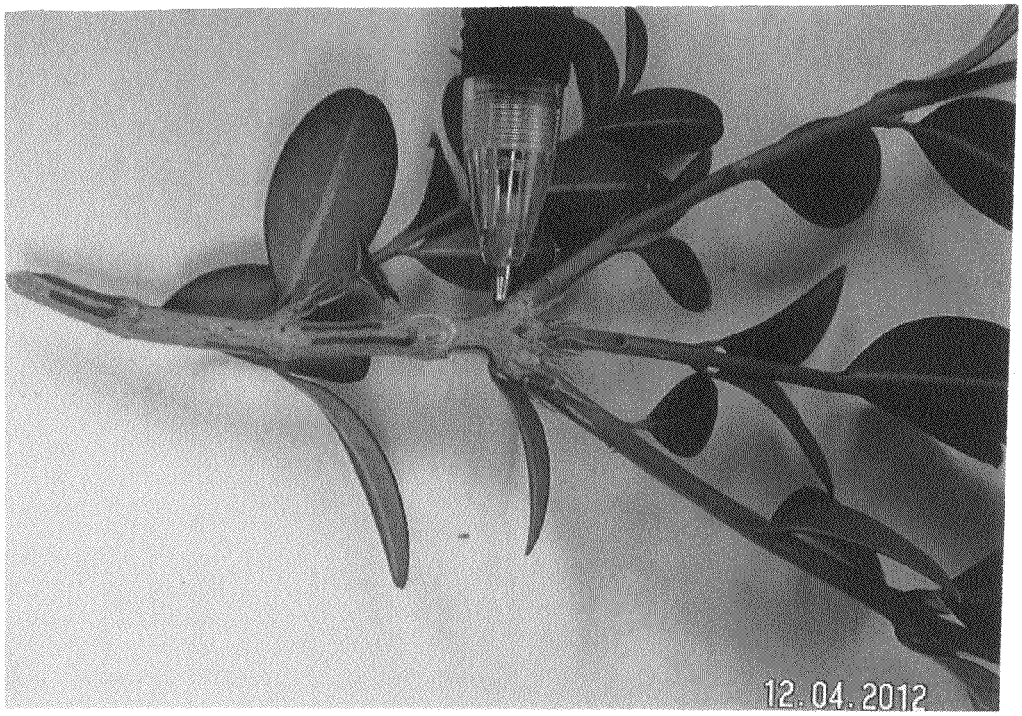

FIG. 8 illustrates a typical branch of the new cultivar in which the transition between one-year-old growth and two-year-old growth is identified by pointing. For ease of viewing, some leaves have been removed. One-year-old growth is present on the right and two-year-old growth is present on the left. The photograph was prepared during early December.

DETAILED DESCRIPTION

The following is a detailed description of the new cultivar of the present invention which was prepared while observing plants growing in full sun during November at Piney River, Va., U.S.A. Such plants had been asexually reproduced by the rooting of cuttings. Color terminology is in accordance with The R.H.S. Colour Chart of The Royal Horticultural Society, London, England (1995 Edition or equivalent). General color terms are to be accorded their customary dictionary significance.

Type: Hardy broad-leafed woody evergreen shrub for garden decoaration and general landscape usage.

Botanical classification: *Buxus sempervirens*, c.v. Thomas Jefferson, of unknown parentage.

Growth habit: Taller than wide, dense, upright, substantially uniform presentation of branches. When compared to the 'Dee Runk' cultivar, the new cultivar is a less rapid grower, displays sturdier branches, and generally is more uniform in overall appearance. When compared to the 'Green Mountain' cultivar, the new cultivar is narrower at the base and displays darker green foliage. The new cultivar does not require pruning to maintain an attractive upright appearance.

Plant dimensions: A twelve-year-old plant commonly is approximately 5 feet in height on average, and approximately 2 feet in width at the widest point on average. A fifteen-year-old plant commonly is approximately 6 feet in height on average, and approximately 3 feet in width at the widest point on average. At thirty years of age a height of approximately 12 feet on average and width of approximately 6 feet on average is anticipated.

General appearance: Attractive dense upright grower with rich dark green leaf coloration wherein the foliage coloration is well maintained throughout the year. The foliage fills in nicely.

Growth rate: Medium growing with average vigor. New foliage commonly is formed at a rate of approximately 4 to 6 inches per year. Commonly a spring flush in April to May of approximately 3 to 5 inches is produced followed commonly by additional growth of approximately 1 inch in the late summer to early fall.

Branches: Sturdy of superior strength and rigidity, nevertheless supple and often capable of substantial bending without breakage, and commonly resist snow and ice damage during the winter months. Branches commonly emerge at angles of approximately 45° which is a considerably greater angle than displayed by the also upright 'Dee Runk' cultivar. Juvenile branches are smooth in texture and commonly are near Green Group 138B in coloration. After the first year, branches commonly display scaly rough light brown bark that is near Greyed-Orange Group 165D in coloration sometimes including green striations parallel to the stem length of near Green Group 138A. Branch roughness tends to increase with age. One-year-old branches commonly are approximately 2 to 2.5 mm in diameter. This compares to a one-year-old diameter of approximately 1.5 to 2 mm commonly observed for *Buxus sempervirens* Common Boxwood. Two-year-old branches of the new cultivar commonly are approximately 3 to 4 mm in diameter. This compares to a two-year-old diameter of approximately 2 to 3 mm commonly observed with *Buxus sempervirens* Common Boxwood.

Figure 1:
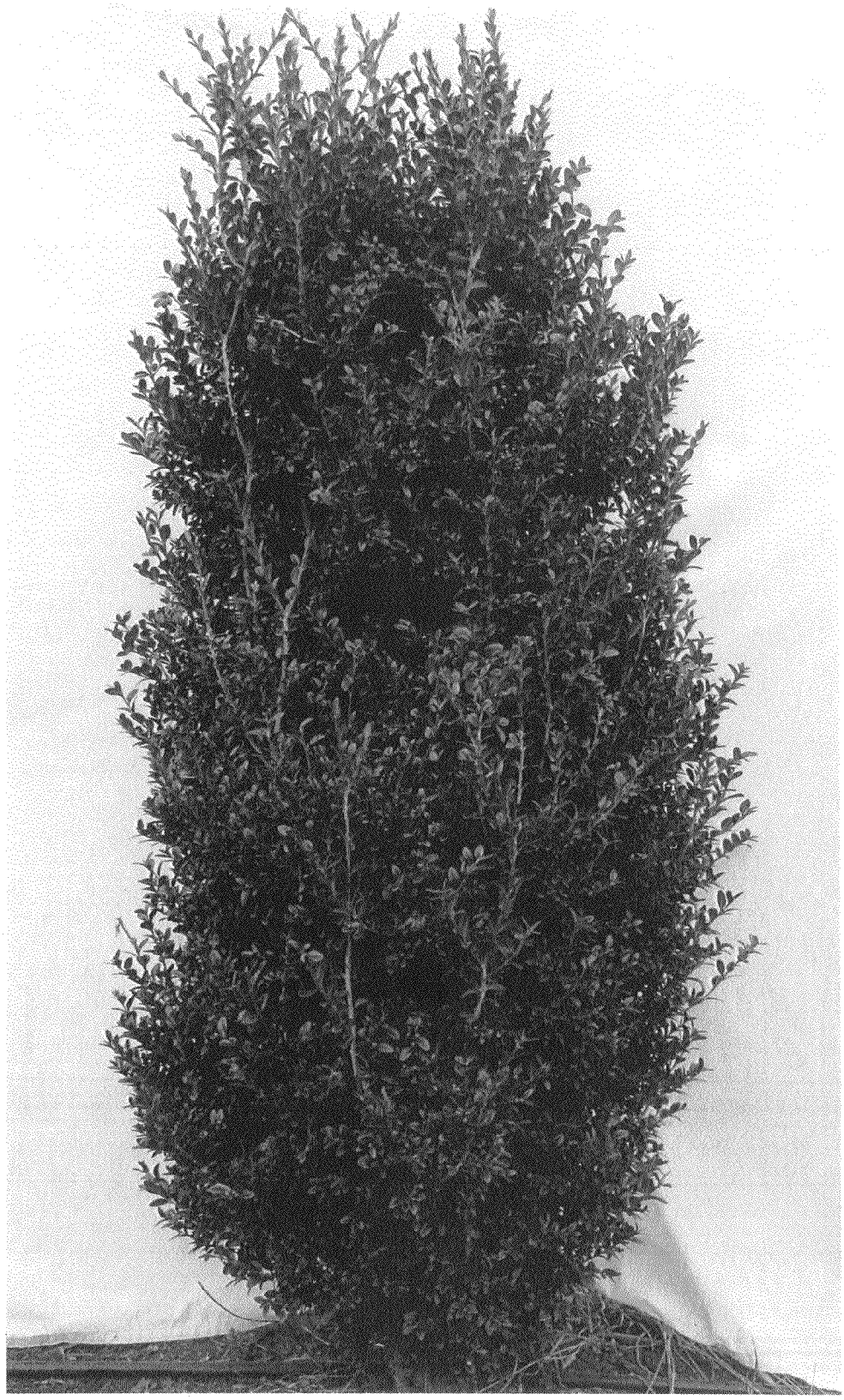
Figure 2:
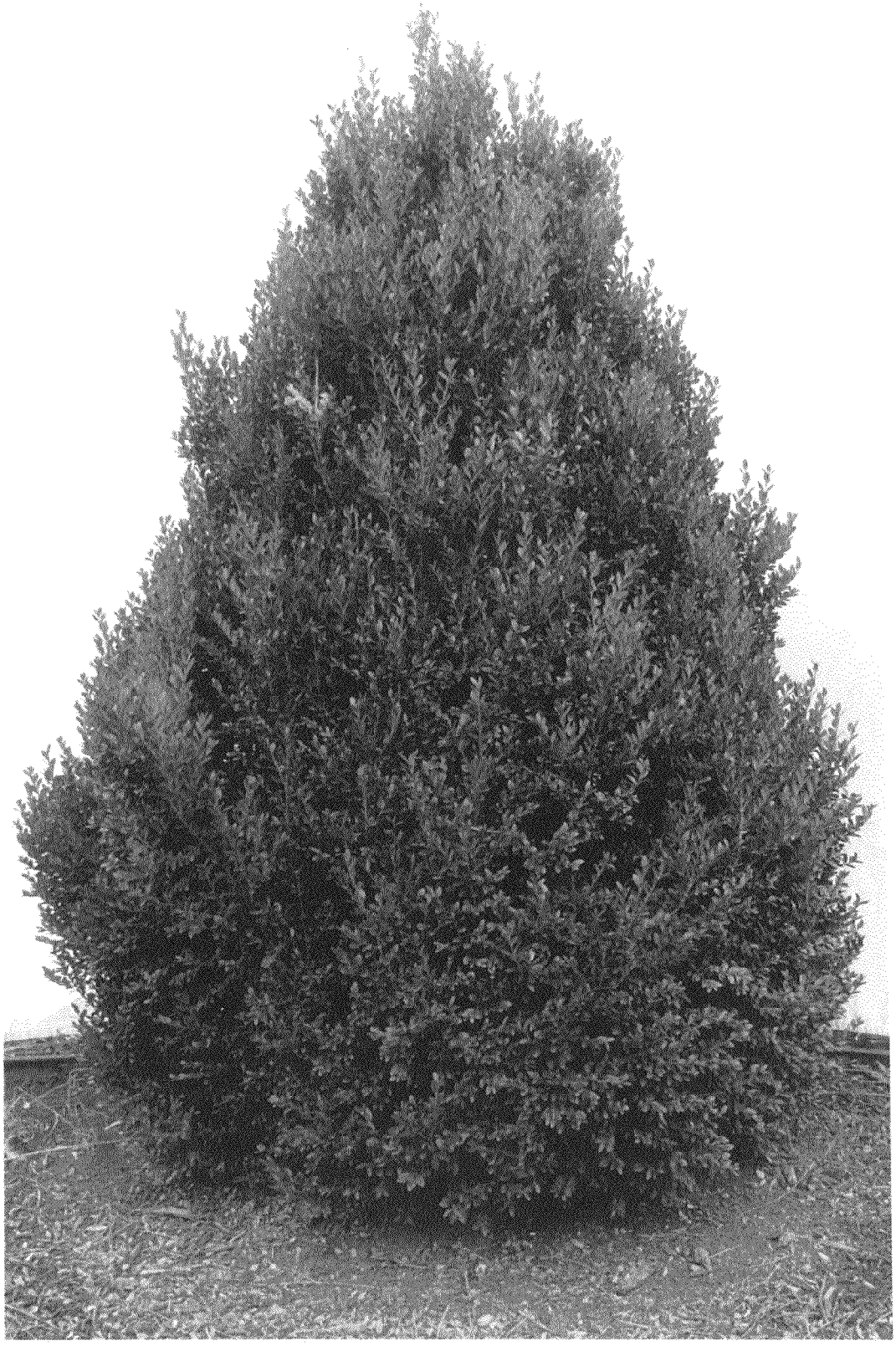
Figure 3:
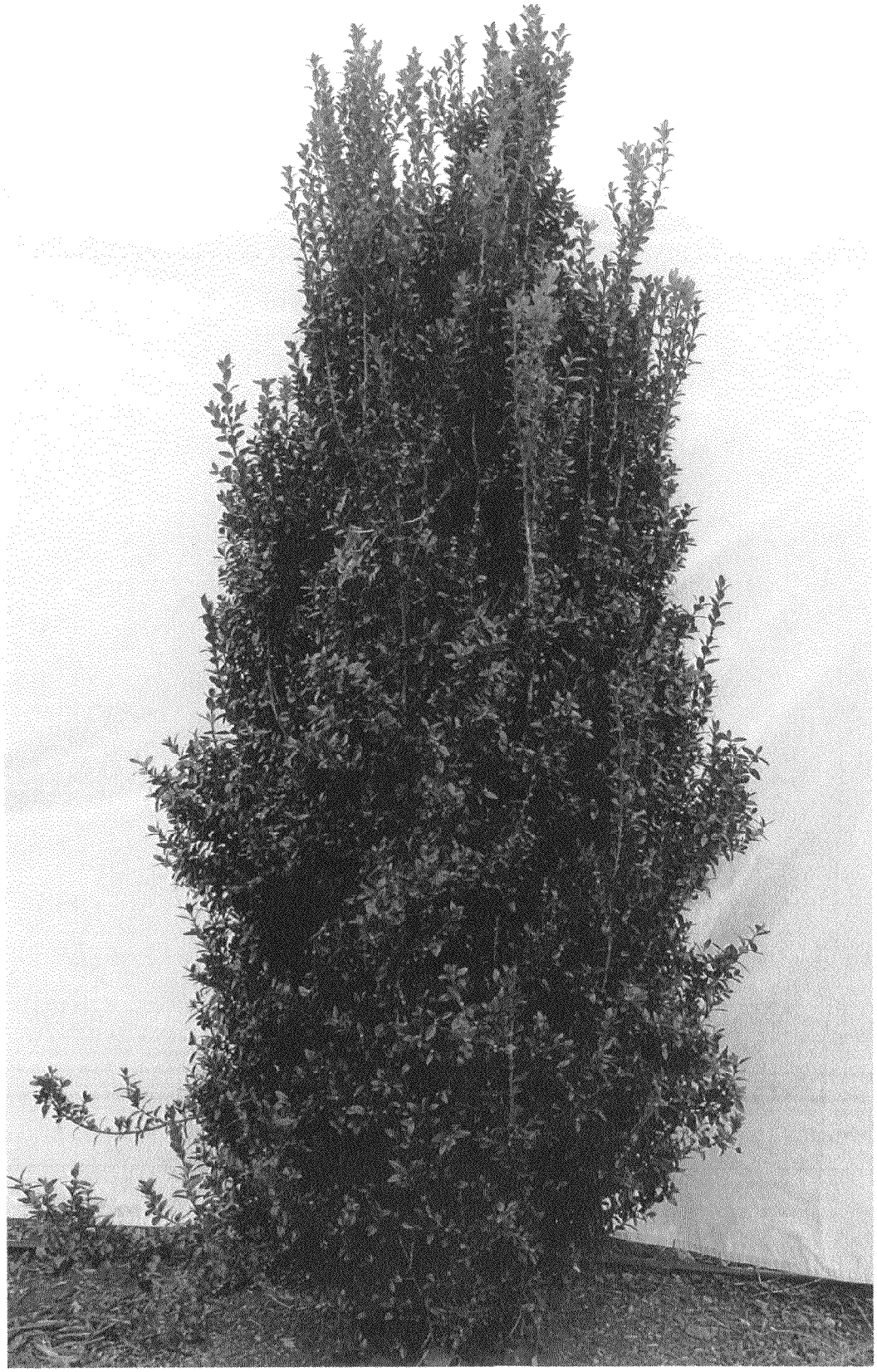
Figure 4:
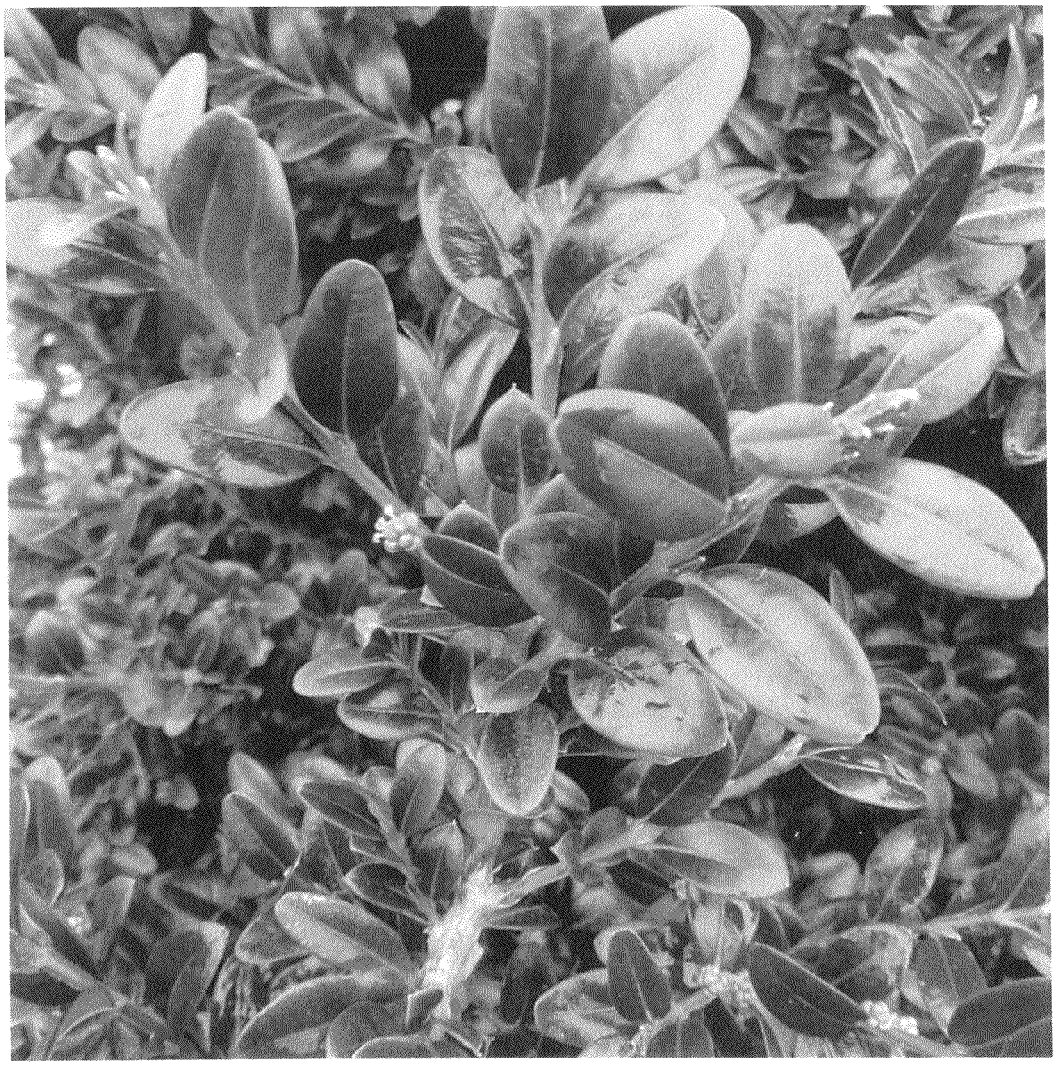
FIG. 4 illustrates typical foliage and branches of the new cultivar. The glossy upper leaf surfaces are apparent as are newly formed vegetative buds which will form foliage during the following spring.
Figure 5:
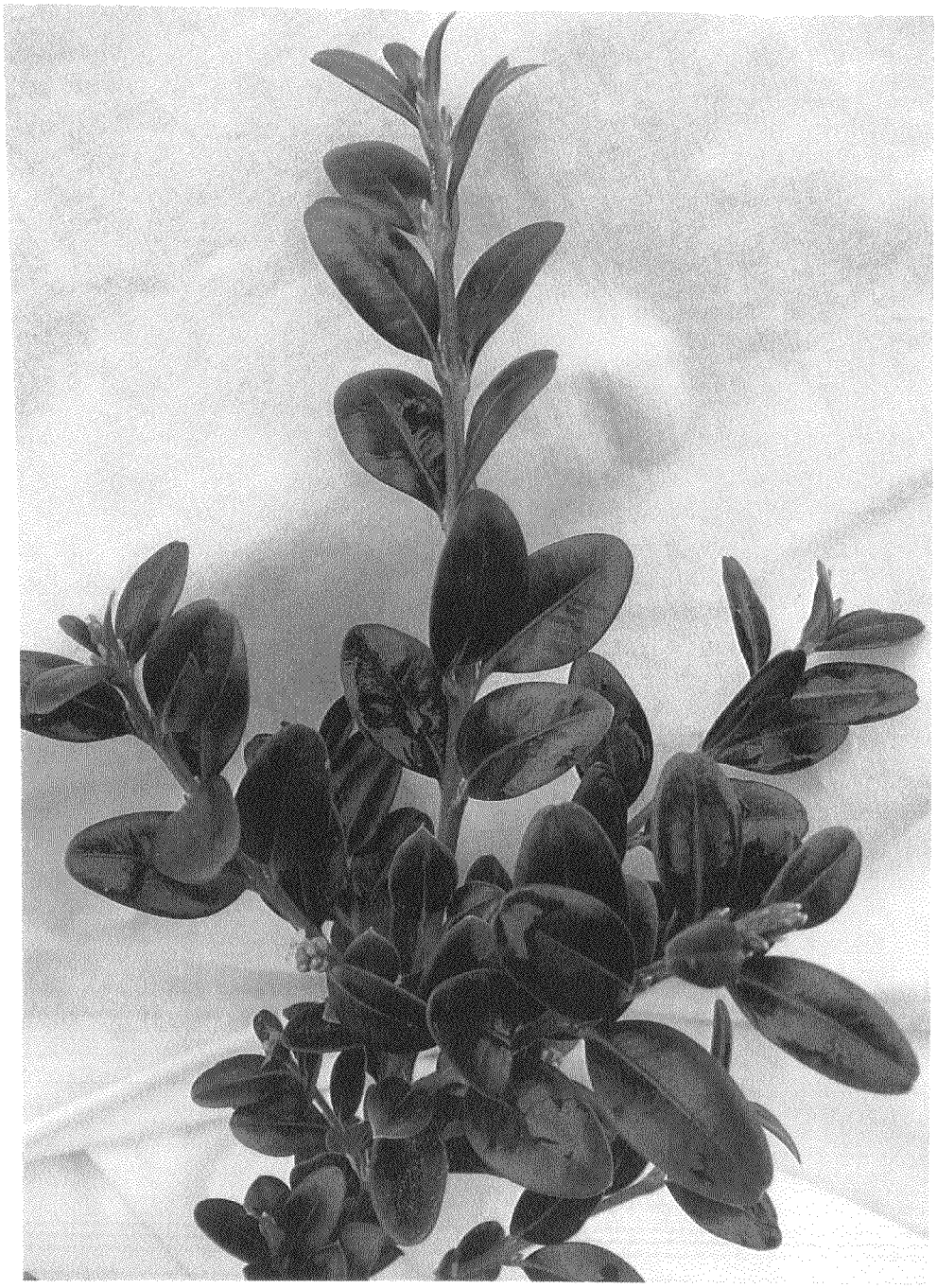
FIG. 5 illustrates a close view of typical foliage and branches of the new cultivar wherein the typical leaf configuration and the glossiness of the upper leaf surfaces are shown.
Figure 6:
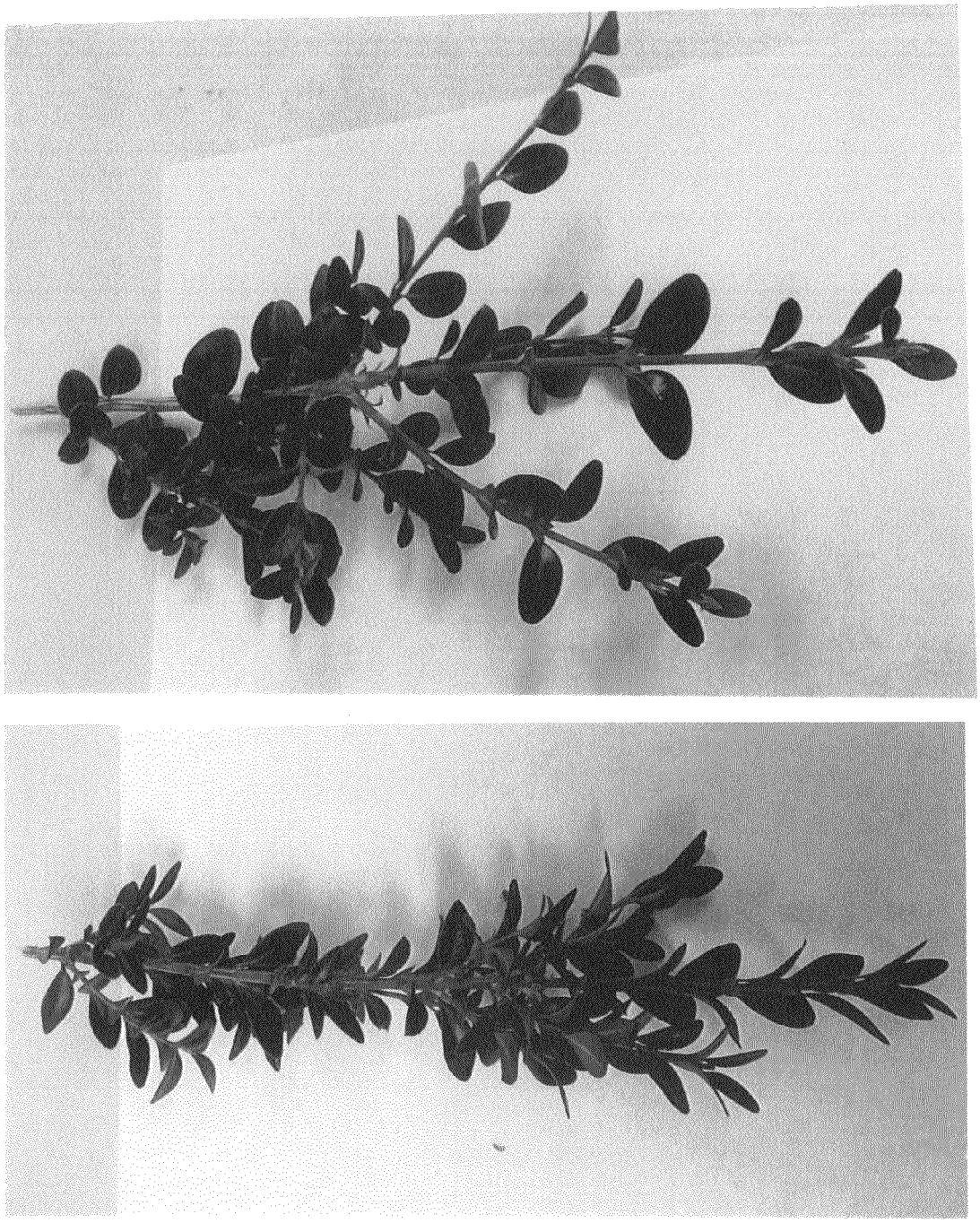
FIG. 6 illustrates for comparative purposes above a typical branch of the new cultivar and below a typical branch of Common Boxwood (*Buxus sempervirens*). The new cultivar displays a deeper green leaf coloration and commonly more spacing between leaves as they are disposed along the stem.

Foliage: Decussate leaf arrangement, generally elliptic to narrowly-ovate in shape, retuse to sometimes rounded apex, cuneate to obtuse base, entire margins, commonly approximately 18 to 28 mm in length on average, approximately 8 to 16 mm in width on average, rich dark green near Green Group 139A in coloration on the upper surface, and near Green Group 138B in coloration on the under surface. Accordingly, the leaf size commonly is somewhat larger than that often displayed by *Buxus sempervirens* Common Boxwood. The green leaf coloration of the new cultivar is considerably darker than that of the 'Green Mountain' cultivar. The upper leaf surfaces commonly are glossy (i.e., between semi-glossy and full glossy). The adjacent leaves commonly are spaced along stems at greater distances than commonly observed with other *Buxus sempervirens* cultivars. See, for instance, FIG. 6 where a leaf spacing comparison with the Common Boxwood is shown. Typical distances between adjacent leaves on a stem commonly are approximately 12 to 25 mm on average for the new cultivar compared to approximately 8 to 15 mm often displayed by Common Boxwood. The glossiness of upper leaf surfaces commonly is slightly more than that of the 'Green Mountain' and 'Dee Runk' cultivars. Glossiness is absent on the under leaf surfaces. The leaf petioles are extremely short as illustrated. Pinnate venation is displayed as illustrated.

Inflorescence: Under conventional plant nursery growing conditions in which good cultural practices are utilized to produce strong healthy plants, only rare sporadic flowering is observed. When present, the inconspicuous flowers open during early spring. Such flowering is believed to be more pronounced when plants of the new cultivar are subjected to stress. No flowers or seeds are available for further characterization. In the infrequent instances when flowering occurs, based on available information, such flowering is believed to resemble that of *Buxus sempervirens* Common Boxwood.

Asexual reproduction: The new plant is well capable of asexual reproduction via the use of stem cuttings during late summer into winter. Also, layering has been utilized wherein a branch is caused to contact the ground, is allowed to root where contact is made with the ground, and subsequently is severed from the original plant. Following asexual reproduction through the rooting of a cutting, it commonly takes approximately 18 months to produce a well-rooted plant suitable for planting out. It commonly requires approximately 4 years to produce a marketable plant of the new cultivar having a height of 2 feet following asexual reproduction through the rooting of a cutting.

Hardiness: The new cultivar has displayed good winter hardiness at Greenville, S.C., U.S.A., and Piney River, Va., U.S.A. Winter temperatures as low as 10° F. have been well tolerated. The plant is believed to be winter hardy in at least U.S.D.A. Hardiness Zone Nos. 5 to 8.

Disease tolerance: During observations to date, the disease tolerance of the new cultivar has been outstanding with no particular disease problems having been encountered. The plant has well withstood diseases that sometimes attack Common Boxwood. When the new cultivar was tested for susceptibility to the recently discovered Boxwood disease *Cylindrocladium buxicola*, it was found to have better resistance than many other *Buxus sempervirens* cultivars.

Pest tolerance: No particular insect problems have been encountered during observations to date. During a three-year study, the new cultivar has been determined to be one of the most resistant Boxwood plants known to Boxwood Leafminer, *Monarthropalpusi flavus* (Schrank). This is considered to be of prime importance, since Boxwood Leafminer often has been considered to be a prime enemy of previously available *Buxus sempervirens* plants.

Plants of the new 'Thomas Jefferson' cultivar have not been observed under all possible environmental conditions to date. Accordingly, it is possible that the phenotypic expression may vary somewhat with changes in light intensity and duration, cultural practices, and other environmental conditions.

The invention claimed is:

1. A new and distinct Boxwood plant having the following combination of characteristics:

(a) displays a pronounced upright growth habit, (b) displays throughout the year attractive deep green leaves having a glossy upper surface in the substantial absence of winter bronzing, (c) forms branches of superior strength that commonly will resist snow and ice damage during winter months, (d) displays good resistance to disease and insects, and (e) is particularly well suited for providing distinctive ornamentation in the landscape;

substantially as illustrated and described.

* * * * *